United States Patent [19]

Brenner et al.

[11] Patent Number: 5,634,923
[45] Date of Patent: Jun. 3, 1997

[54] SAFETY FILTER FOR AN OPHTHALMIC THERAPEUTIC AND/OR DIAGNOSTIC INSTRUMENT

[75] Inventors: Roland Brenner, Wallhausen; Josef Schlosser, Jagstzell; Peter Reimer, Ellwangen, all of Germany

[73] Assignee: Carl-Zeiss-Stiftung, Heidenheim, Germany

[21] Appl. No.: 406,411

[22] Filed: Mar. 20, 1995

[30] Foreign Application Priority Data

Mar. 19, 1994 [DE] Germany .................. 44 09 506.6

[51] Int. Cl.⁶ ............................................. A61N 5/06
[52] U.S. Cl. .................. 606/10; 606/4; 606/13; 351/213
[58] Field of Search ................. 606/2, 3–18; 351/206, 351/209, 211, 215

[56] References Cited

U.S. PATENT DOCUMENTS

| | | |
|---|---|---|
| 4,520,816 | 6/1985 | Schachar et al. . |
| 4,753,525 | 6/1988 | Gaul et al. .................... 350/526 |
| 4,865,441 | 9/1989 | Reis . |
| 5,042,939 | 8/1991 | Zayek ............................ 351/206 |
| 5,300,062 | 4/1994 | Ueno ............................. 606/4 |
| 5,342,351 | 8/1994 | Blaha et al. ................... 606/4 |

*Primary Examiner*—David M. Shay
*Attorney, Agent, or Firm*—Walter Ottesen

[57] ABSTRACT

The invention is directed to a safety filter for an ophthalmic therapeutic and/or diagnostic unit into which a laser beam is coupled for therapeutic purposes. The safety filter is optically dimensioned in such a way that no change in the focal intercept results when the filter is swung into the viewing beam path. The filter largely absorbs the particular laser wavelength.

11 Claims, 3 Drawing Sheets

SAFETY FILTER FOR AN OPHTHALMIC THERAPEUTIC AND/OR DIAGNOSTIC INSTRUMENT

FIELD OF THE INVENTION

The invention relates to a safety filter which absorbs defined wavelengths and is integrated in a laser adapter. The laser adapter is used to couple a laser beam into an ophthalmic therapeutic and/or diagnostic instrument for therapeutic purposes. The invention also relates to a laser adapter having an attachment mechanism for mounting on an ophthalmic therapeutic and/or diagnostic instrument.

BACKGROUND OF THE INVENTION

Not only slit lamps used solely for diagnostic purposes, but also so-called laser slit lamps are known in ophthalmology. The optical configuration of these laser slit lamps is always such that it allows the therapeutic use of suitable laser wavelengths in the patient's eye. In addition to other optical components, standard laser slit lamps feature a safety filter in the viewing beam path of the slit lamp microscope in order to absorb as much of the laser radiation as possible. This prevents reflected laser radiation from reaching the eye of the physician and putting him at risk.

Conventional diagnostic slit lamps which do not offer any possibility of laser treatment normally do not feature such a safety filter.

Various manufacturers are now providing retrofit kits which allow the conversion of conventional diagnostic slit lamps into laser slit lamps using a so-called laser adapter. When a laser adapter is retrofitted to a conventional diagnostic laser slit lamp, a suitable safety filter for the physician must also be provided for safety reasons.

Various possibilities exist for mounting such a safety filter in the laser adapter. It is possible, for example, to mount this safety filter as a stationary unit at a defined point in the viewing beam path of the slit lamp. This has the disadvantage that the physician always looks through this filter at the treatment site irrespective of whether the laser has been activated or not. This safety filter has an absorbing effect usually in a wavelength range between 460 to 540 nm. For this reason, a pronounced color distortion in the visible spectral range results, however, with such a safety filter. The above wavelength range is always filtered out of the visible spectral range, resulting in an orange-colored image for the physician. This color distortion is perceived to be irritating.

A known alternative uses a motor to pivot the safety filter into the beam path only during the actual laser treatment, that is, when the laser is active. Thus, the color distortion described above is only present during the actual laser treatment. If such a pivotable safety filter is to be provided in a laser adapter retrofitted to conventional diagnostic slit lamps, the only possibility is to swing in the safety filter between the objective lens or the two objective lenses of the slit lamp microscope and the observed target plane when the laser has been activated.

U.S. Pat. No. 4,520,816, for example, illustrates the prior art pertinent for this type of arrangement and is incorporated herein by reference. If, in the arrangement disclosed in this patent, the safety filter is swung into this position in the viewing beam path of the slit lamp microscope when the laser is activated, the focal intercept of the optical system of the slit lamp microscope will be changed for as long as the filter remains in the beam path. During this period, the physician will see a blurred image, and a degree of uncertainty may result for focusing the laser beam on the target plane which must be done with high precision.

SUMMARY OF THE INVENTION

In view of the above, it is an object of the invention to provide a safety filter and a laser adapter for an ophthalmic therapeutic and/or diagnostic unit which avoids the disadvantages of the prior art.

The safety filter assembly of the invention is for absorbing a defined wavelength in an ophthalmic therapeutic and/or diagnostic instrument. The instrument has an optical system defining a focal intercept and includes viewing optics and an objective conjointly defining a viewing beam path leading to a target plane and the instrument further is equipped with a device for coupling a laser beam into the viewing beam path for therapeutic purposes. The safety filter assembly includes: a safety filter; displacing means for holding and displacing the safety filter between a first position outside of the beam path and a second position in the beam path between the objective and the target plane; and, the safety filter being dimensioned so as to cause the focal intercept to remain unchanged when the safety filter is moved into the second position.

The use of an optically corrected safety filter now ensures that the physician also obtains a sharp image when the safety filter is in the beam path. This avoids any possible uncertainty as to focusing which could produce a blurred image caused by a safety filter according to the prior art. The optical efficacy of the safety filter is selected such that no change results in the focal intercept of the viewing optics of the slit lamp microscope when the filter is swung into the beam path.

The use of suitable plastic materials ensures that a safety filter according to the invention can be cost-effectively produced. Here, plastic materials as they are also used for spectacle lenses, for example, can be used in an advantageous manner.

The laser adapter of the invention also allows conventional laser slit lamps of different makes to be modified without the disadvantages specified above. In particular, it is not necessary to intervene in the viewing optics of the diagnostic slit lamp because the safety filter of the laser adapter is suitably positioned between the patient and the viewing optics of the slit lamp microscope and is pivoted in utilizing a motor.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
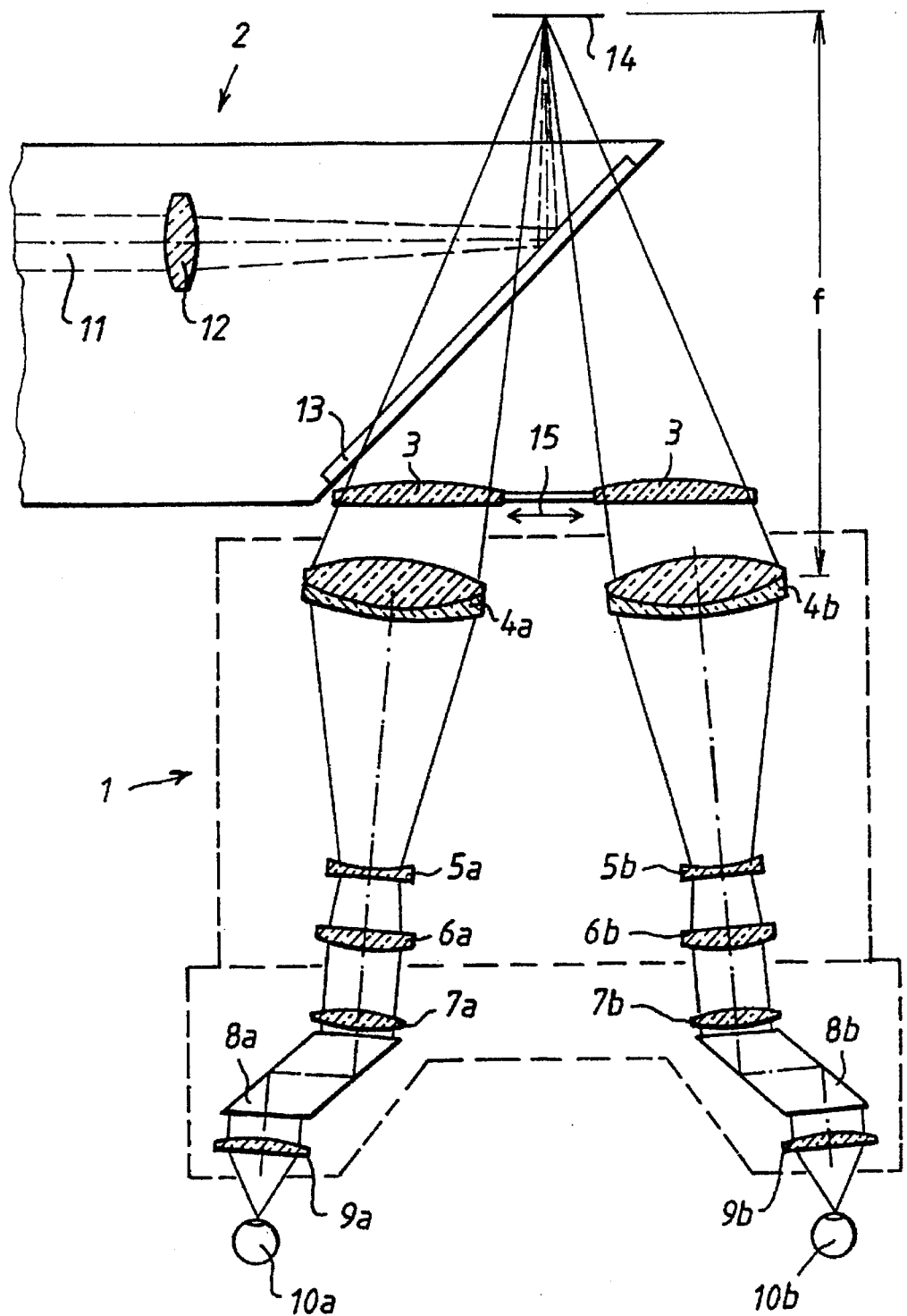
FIG. 1 shows a schematic of the beam paths in an embodiment of the laser adapter according to the invention including the safety filter according to the invention.

FIG. 1 is a schematic view of the different beam paths in an embodiment of the laser adapter according to the invention in a plan view.

The illustration shows the diagnostic slit lamp including the slit lamp microscope 1 with its two stereoscopic viewing beam paths including the optical components required. Not shown in FIG. 1 is the slit illumination system which is configured in a manner known per se.

The stereoscopic viewing beam paths each include one objective lens (4a, 4b), followed by a number of further optical components (5a, 6a, 7a, 8a, 9a; 5b, 6b, 7b, 8b, 9b) such as lens elements and deflecting prisms, which are arranged in front of the eyes (10a, 10b) of the viewer. This type of diagnostic slit lamp is marketed, for example, by Carl Zeiss or by the Haag-Streit Company.

As set forth above, this type of slit lamp does not offer any capability of laser application in the patient's eye. The laser adapter according to the invention is for retrofitting a diagnostic slit lamp to impart this capability thereto.

FIG. 1 shows components of the laser adapter 2 according to the invention including the safety filter 3 of the invention. In FIG. 1, the housing 2a of the laser adapter 2 with its optical component 12 in the laser beam path 11 is shown shifted by 90° for greater clarity, that is, this housing 2a is actually positioned perpendicularly to the drawing plane and extends perpendicularly to the stereo base of the viewing beam paths. The laser adapter 2 also includes a radiation source (not shown) in the form of a laser providing a suitable laser wavelength.

If a radiation source of a compact configuration is used, that is, a laser diode, this radiation source could also be accommodated in the housing 2a of the laser adapter. Here, there is a possibility of using laser diodes which provide laser radiation in the wavelength range between 600 and 700 nm.

Alternatively, the radiation source can be positioned outside the housing 2a and its light conducted to the housing 2a by means of fiber optic light conductors. If, for example, an argon ion laser in the wavelength range between 460 nm and 540 nm is used as the radiation source, the use of fiber optic light conductors for the light supply is a practical alternative. The radiation source necessary for the laser adapter of the invention can therefore be positioned as described for the two embodiments.

The housing 2a provides various optical components which are used for beam dimensioning and/or focusing on the target plane in a manner known per se. Of these optical components, such as Galilean beam expander optics, focusing lens, et cetera, only a single lens 12 is shown. The laser beam 11 passes through these optical components and reaches the deflecting mirror 13 in the laser adapter which is arranged in front of the two objective lenses (4a, 4b) of the viewing optics of the slit lamp microscope 1. The deflecting mirror 13 directs the laser beam 11 to the viewing plane or target plane 14 in the eye of the patient. For this purpose, it is advantageous to apply a wavelength-selecting coating to the deflecting mirror in such a way that the particular laser wavelength used is largely reflected in the direction of the target plane 14.

The dimensions of the deflecting mirror 13 are selected so that the projection of the deflecting mirror on the entrance plane of the slit lamp microscope 1 completely covers the component stereoscopic beam paths. For this reason, the wavelength-selecting coating of the deflecting mirror 13 in itself prevents a large portion of the harmful laser radiation reflected from the target plane from reaching the viewing optics of the diagnostic slit lamp 1. This already provides a certain protection for the physician.

According to the invention, a safety filter 3, which is pivoted in by a motor, is provided in the two stereoscopic beam paths of the slit lamp microscope 1. As soon as the laser is activated, that is, when the laser is enabled in the direction of the patient's eye, the safety filter 3 is automatically pivoted into the beam path and, in combination with the wavelength-selecting coating of the deflecting mirror 13, prevents harmful laser radiation from being reflected back into the eye of the physician while the laser is active. The arrow 15 in FIG. 1 shows schematically how the safety filter 3 according to the invention is pivoted into and out of the beam paths.

Also apparent in FIG. 1 is that the safety filters 3 in the two stereoscopic viewing beam paths have each been optically dimensioned so that no change in the focal intercept (f) occurs in the slit lamp microscope 1 when the filters are swung into the viewing beam paths. Unlike the use of a flat plate, the beam is not offset and hence no blurred image results for the viewer when the safety filter 3 has been swung into position.

The embodiment of FIG. 1 includes separate component safety filters in the two stereoscopic viewing beam paths, respectively. This is, however, by no means required; instead, the safety filter of the invention having an optically correcting effect can be configured in the form of a single optical component common to both viewing beam paths.

It will now be explained how an embodiment of the safety filter 3 according to the invention must be optically dimensioned in order to compensate for a change in the focal intercept occurring in the viewing beam paths of the slit lamp microscope. This change in focal intercept is caused when the safety filter is swung into position.

A calculation is first made to determine the extent to which the focal intercept changes in the viewing beam paths if a flat plate with a defined thickness and of a defined material is used as a safety filter and swung into the viewing beam paths of the slit lamp microscope. The resultant change $\delta f'$ in the focal intercept is obtained using the following equation (i):

$$\delta f' = d \left[ 1 - \frac{\cos \epsilon}{\sqrt{n^2 - \sin^2 \epsilon}} \right] \quad (i)$$

wherein: d: thickness of the flat plate;
ε: angle of incidence; and,
n: refractive index of the flat plate.

According to equation (i), when the flat plate is brought into the stereoscopic viewing beam paths, a change in the focal intercept of $\delta f'=0.84$ mm results for a diagnostic slit lamp with an objective lens focal intercept of f'=91 mm, a stereo angle of 13° (that is, ε=6.5°), a refractive index of the flat plate of n=1.50 (material of the flat plate is CR 39) and a flat plate thickness ws of d=2.5 mm. Thus, the focal intercept increases by 0.84 mm, that is, the position of the focal plane is displaced away from the viewer by this amount thereby, in turn, causing a blurred image for the physician.

According to the invention, this change in focal intercept must be compensated for by appropriately dimensioning the safety filter. This is achieved in the embodiment having the above data by inserting a safety filter with a collecting optical power into the beam path. This safety filter should be configured as a plane-convex or biconvex lens. The following will explain how the required optical power of the safety filter is determined based on the data given above.

For neighboring thin lens elements, the following equation (ii) is usually valid for the vertex power $S'_{total}$ of the system:

$$S'_{total} = S_1' + S_2' \quad (ii)$$

Hence, the vertex dioptric power $S'_{total}$ of the entire system equals the sum of the two individual vertex dioptric powers.

The vertex power $S'_{new}$ of the overall system changed by the safety filter when swung into position is obtained by:

$$S'_{new}=1/(f'+\delta f')$$

If the above values are inserted for f' and δf', a modified dioptric power $S'_{new}$=10.8885 D is obtained when the physician safety filter is swung into the beam path.

Using a desired vertex dioptric power $S'_{des}$=1/f'=10.989 D corresponding to the vertex dioptric power without a safety filter, the vertex power S' of the swing-in safety filter is obtained with the equation (ii) as:

$$S'=S'_{des}-S'_{new}$$

With the above numerical values, a required vertex dioptric power S' of the safety filter of S'=0.1005 D results corresponding to a focal intercept $f_s$ of the safety filter of 9,949.2 mm.

If a plane-convex lens is used as the safety filter, the radius r of the convex surface required is determined by:

$$r=f_s*(n-1).$$

Using the values mentioned above for $f_s$ and n for CR 39, a value of r=4,974.58 mm is obtained for the radius of the convex surface of a plane-convex lens.

In precisely the same way as in this example, the optical values necessary for the optically corrected safety filter according to the invention have to be determined for other conditions.

Figure 2:
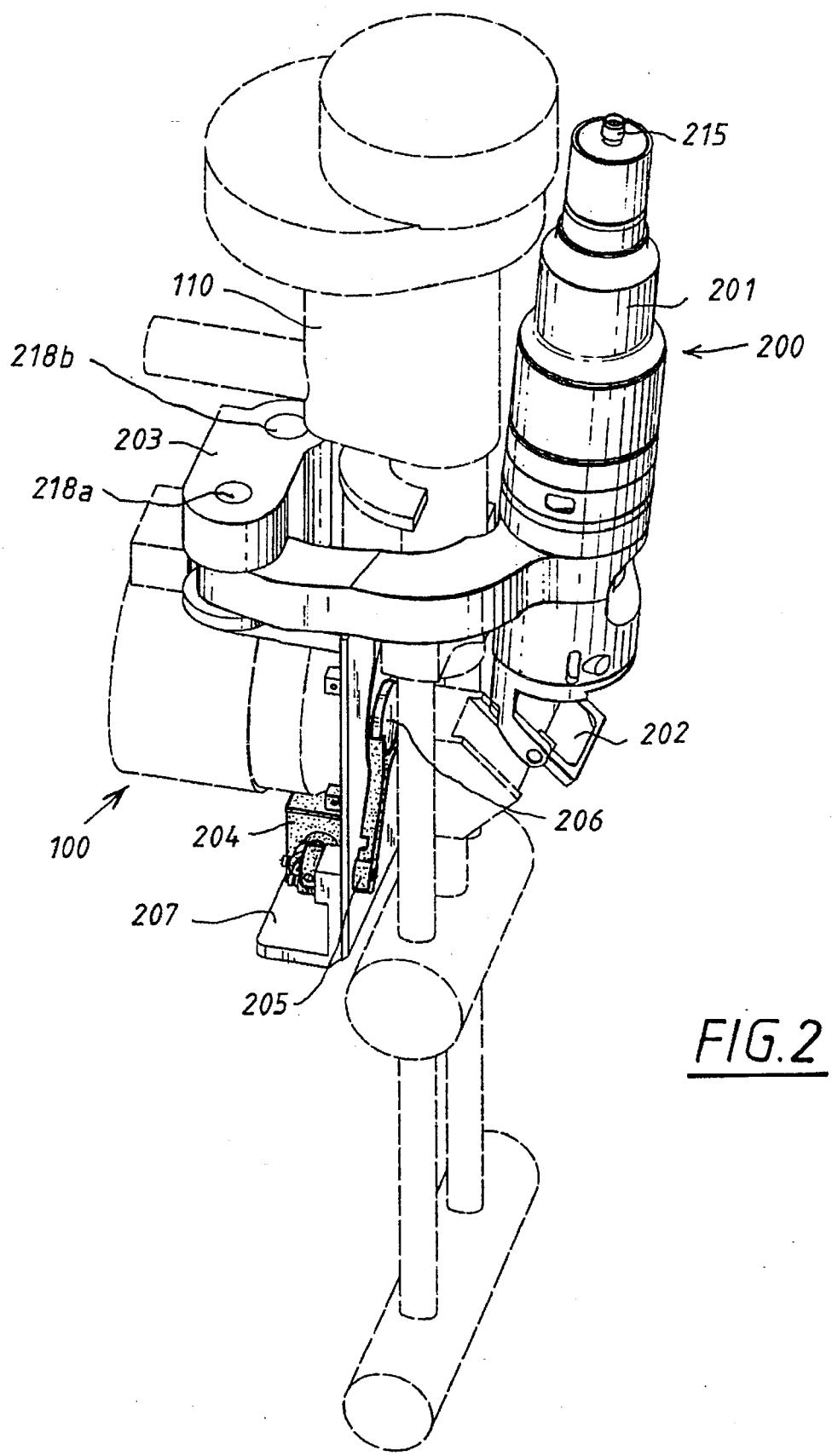
FIG. 2 is a perspective view of an embodiment of the laser adapter according to the invention including a swing-in safety filter with the adapter being mounted on a conventional diagnostic slit lamp; and, FIG. 3 is a detail front elevation view of the laser adapter according to the invention shown in FIG. 2.

FIG. 2 is a perspective view showing part of a diagnostic slit lamp including a slit lamp microscope 100 with a slit illumination system and the laser adapter 200 according to the invention mounted on the slit lamp. For greater clarity, dashed lines have been used to illustrate the parts of the diagnostic slit lamp, while the laser adapter 200 is shown in solid lines. Unlike FIG. 1, the housing 201 of the laser adapter 200 including the radiation source and the optical components is correctly oriented to the diagnostic slit lamp, that is, perpendicularly to the stereo base of the viewing beam paths.

The embodiment of the laser adapter 200 shown comprises a housing 201 which accommodates the optical components specified above for the dimensioning and/or focusing the beam.

The radiation source used is an argon ion laser (not shown) having an output radiation in the wavelength range of 460 nm to 540 nm. This output radiation is conducted by optical fibers (not shown) and is coupled via an interface 215 into the housing 201 of the laser adapter 200.

Below the housing 201, a deflecting mirror 202 with the wavelength-selecting coating described is provided on the laser adapter to deflect the laser beam towards the target plane. After deflection, therefore, the laser beam travels in the same direction as the two stereoscopic viewing beam paths of the slit lamp microscope 100.

The wavelength-selecting coating of the deflection mirror 202 reflects the laser wavelengths of the laser light in the spectral range of 460 nm to 540 nm to as great an extent as possible.

The attachment mechanism 203 comprising several components allows the mounting and removal of the laser adapter 200 on the diagnostic slit lamp. These components include the illumination unit 110 of the slit lamp 100. Two bores (218a, 218b) are provided in the attachment device 203 on the side facing away from the patient and two attachment pins precisely engage corresponding ones of the bores. The two attachment pins are mounted on the upper part of the housing of the slit lamp 100. These attachment pins are provided on conventional slit lamps in order to mount other accessories, such as a tonometer, on the slit lamp.

A support plate 207 in front of the objective lenses of the slit lamp microscope 100 is associated with the attachment mechanism 203. The support plate 207 is used to mount the motorized swing-in safety filter 206 so that it can be placed at a defined position in the stereoscopic viewing beam paths.

When the laser is activated, the safety filter 206 is swung in front of the two objective lenses of the diagnostic slit lamp 100 by an electromotor-operated pull magnet 204 via a lever system 205. The pull magnet 204 and the lever system 205 are also mounted on the support plate 207.

Figure 3:
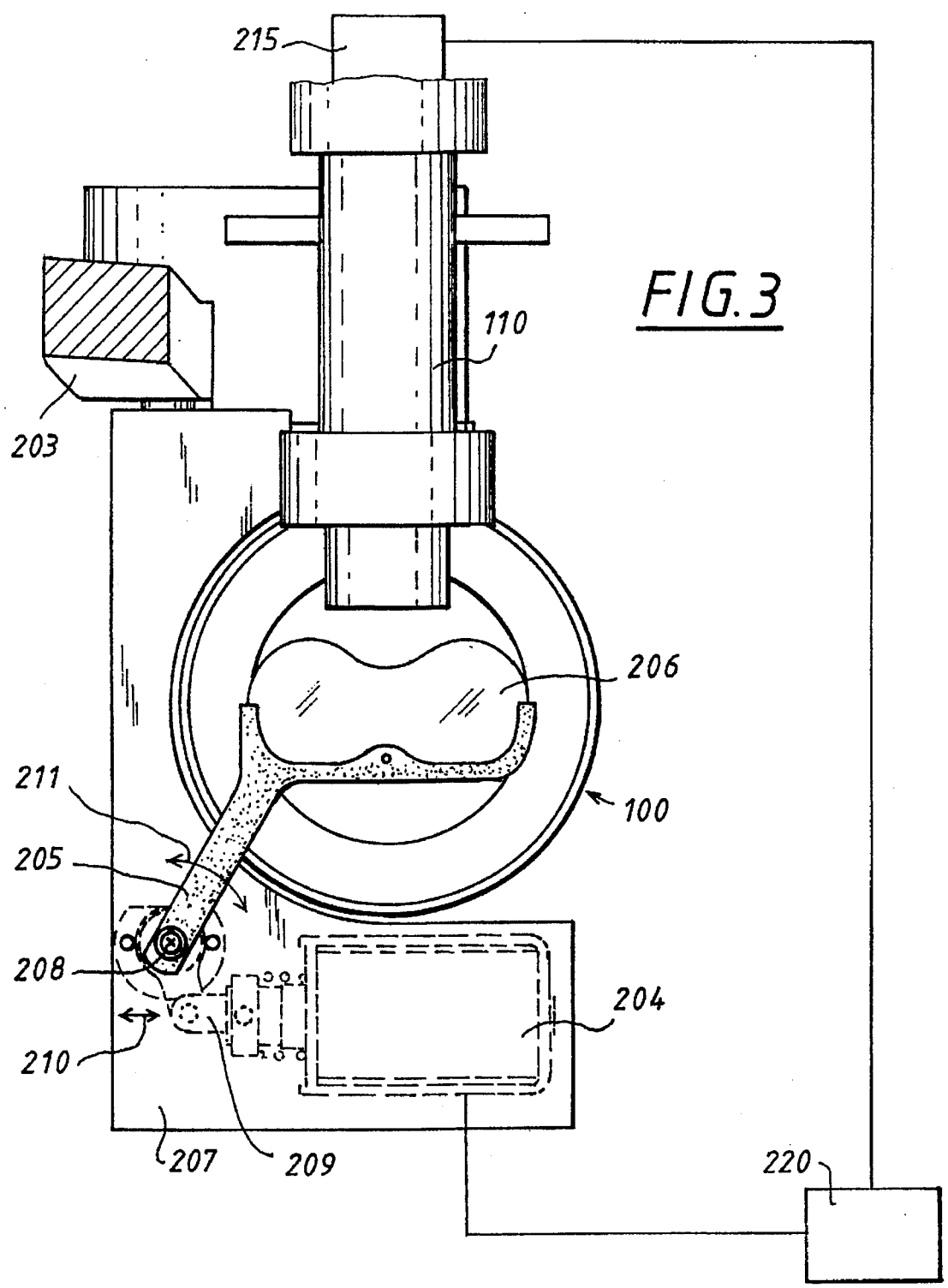

FIG. 3 shows a partial front elevation view of the embodiment of the device shown in FIG. 2. This illustration does not show the housing of the laser adapter and its deflecting mirror as shown in FIG. 2. However, the slit illumination system 110 of the diagnostic slit lamp is now clearly visible.

In front of the objective lenses of the slit lamp microscope 100 (only partially visible), this illustration clearly shows the motorized, swing-in safety filter 206 including the attachment mechanism and support plate 207, the pull magnet 204 and the lever system 205 which allows the safety filter 206 to be swung in and out of the beam path.

The pull magnet 204 operates in such a way that, when the laser 215 is activated or deactivated, the piston 209 of the pull magnet is moved in the horizontal direction indicated by the arrow 210 in FIG. 3. The piston 209 of the pull magnet is, in turn, connected to a three-part lever system 205 in such a way that the safety filter is swung in and out when the piston 209 of the pull magnet is moved in the direction of the arrow 210. In FIG. 3, the resultant pivot movement is indicated by the arrow 211. To activate the pull magnet when the laser is triggered, a suitable electronic drive system 220 is necessary.

The safety filter 206 mounted on the lever system 205 of the embodiment shown has a single-part configuration resembling a spectacles frame and completely covers the two objective lenses of the slit lamp microscope 100 when swung into position as shown in FIG. 3 thereby ensuring that no laser radiation is reflected back towards the viewer.

As an alternative to the embodiment described above, two swing-in safety filters with the optical dimensions specified can be pivotally mounted. In addition, a single safety filter acting on both stereoscopic beam paths can be provided as set forth above.

Likewise, it is also possible to use alternative motorized swing-in mechanisms.

In the selection of the material for the safety filter, the plastic material CR 39, for example, proves to be of advantage. This is alkyl glycol polycarbonate which is also used in the production of plastic spectacle lenses and can therefore be made at a relatively low cost. As an alternative, mineral filter glass, for example, OG glass, marketed by the Schott Company, can be used.

The safety filter is also provided with an appropriate coating which absorbs the radiation in the wavelength range of the laser to the greatest possible extent, while the remaining spectrum is transmitted to as large an extent as possible.

To realize the required wavelength-dependent properties of the safety filter according to the invention, the safety filter can also be designed as a dielectric filter which exhibits the required transmission and absorption characteristics and must display the appropriate optical dimensions.

It is understood that the foregoing description is that of the preferred embodiments of the invention and that various changes and modifications may be made thereto without departing from the spirit and scope of the invention as defined in the appended claims.

What is claimed is:

1. A safety filter assembly for absorbing a defined wavelength in an ophthalmic therapeutic and/or diagnostic instrument, the instrument having an optical system defining a focal intercept and including viewing optics and an objective conjointly defining a viewing beam path of non-parallel rays leading to a target plane at the eye of a patient and the instrument further being equipped with a device for coupling a laser beam of laser radiation into the viewing beam path for therapeutic purposes, the safety filter assembly comprising:

a safety filter;

a displacing device for displacing said safety filter from a first position in said beam path without substituting an optical element therefor and for moving said safety filter to a second position outside of said beam path;

said first position being between the objective and the target plane where the beam path is defined by the non-parallel rays; and, said safety filter being dimensioned so as to cause said focal intercept to remain unchanged when said safety filter is moved into said second position where the non-parallel rays pass through said safety filter.

2. The safety filter assembly of claim 1, wherein the radiation of said laser beam has a predetermined wavelength range; and, said safety filter being substantially opaque to said radiation in said wavelength range.

3. The safety filter assembly of claim 1, wherein the laser radiation of said laser beam has a predetermined wavelength range; said safety filter including a body made of OG glass and a coating formed on said body; and, said coating being substantially opaque to said radiation in said wavelength range.

4. The safety filter assembly of claim 1, wherein the radiation of said laser beam has a predetermined wavelength range; said safety filter including a body made of plastic and a coating formed on said body; and, said coating being substantially opaque in said wavelength range.

5. A laser adapter for an ophthalmic instrument, the ophthalmic instrument having an optical system defining a focal intercept, said optical system including viewing optics and an objective conjointly defining a viewing beam path of non-parallel rays leading to a target plane at the eye of a patient, the laser adapter comprising:

optic guiding means for guiding a laser beam into the viewing beam path;

attachment means for releasably attaching said laser adapter to the ophthalmic instrument;

a safety filter assembly for absorbing a defined wavelength of the radiation of said laser beam; and, said safety filter assembly being mounted on said attachment means and including: a safety filter; a displacing device for displacing said safety filter from a first position in said beam path without substituting an optical element therefor and for moving said safety filter to a second position outside of said beam path;

said first position being between the objective and the target plane where the beam path is defined by the non-parallel rays; and, said safety filter being dimensioned so as to cause the focal intercept to remain unchanged when said safety filter is moved into said second position where the non-parallel rays pass through said safety filter.

6. The laser adapter of claim 5, further comprising a laser light source; and, said laser light source being a laser diode integrated into said laser adapter.

7. The laser adapter of claim 5, said attachment including a holder; and, said displacing device comprising:

lever linkage means pivotally mounted on said holder for pivoting said safety filter between said first and second positions;

solenoid means for actuating said lever linkage to move between said first and second positions; and, interface circuit means for energizing said solenoid means when the laser is switched on to move said safety filter into said second position.

8. The laser adapter of claim 7, the radiation of said laser beam being in a predetermined wavelength range; said ophthalmic instrument defining an entry plane; and, said laser adapter further comprising:

a deflection mirror for deflecting said laser beam into said viewing beam path;

said deflection mirror having a coating formed thereon to reflect substantially all of the radiation of said laser beam within said wavelength range; and, said deflection mirror being mounted so as to cause the projection of said mirror in said entry plane to completely cover said viewing beam path.

9. An ophthalmic therapeutic and/or diagnostic instrument comprising:

an optical system defining a focal intercept and including first and second viewing optics and first and second objectives;

said first viewing optics and said first objective defining a first stereoscopic component beam path of non-parallel rays to a target plane and said second viewing optics and said second objective conjointly defining a second stereoscopic component beam path of non-parallel rays to the target plane;

a device for coupling a laser beam of laser radiation into said component beam paths for therapeutic purposes;

a safety filter;

a displacing device for displacing said safety filter from a first position in said beam path without substituting an optical element therefor and for moving said safety filter to a second position outside of said beam path;

said first position being between the objective and the target plane where the beam path is defined by the non-parallel rays; and, said safety filter being dimensioned so as to cause said focal intercept to remain unchanged when said safety filter is moved into said second position where the non-parallel rays pass through said safety filter.

10. The ophthalmic therapeutic and/or diagnostic instrument of claim 9, wherein: said displacing device includes pivot means for pivoting said safety filter between said first and second positions; and, motor means connected to said displacing device for actuating said displacing device to pivot about said pivot means to move said safety filter between said first and second positions.

11. The ophthalmic therapeutic and/or diagnostic instrument of claim 10, said safety filter having a surface area so as to cause all of said component beams to pass through said safety filter when said safety filter is in said second position.

* * * * *